United States Patent [19]

Paull et al.

[11] Patent Number: 4,590,943
[45] Date of Patent: May 27, 1986

[54] SYSTEM FOR PROVIDING POWER TO PORTABLE DEFIBRILLATOR

[75] Inventors: Mike M. Paull, Seattle; Jerry D. Smith, Everett; Kathleen D. Schoenberg, Carnation, all of Wash.

[73] Assignee: Physio-Control Corporation, Redmond, Wash.

[21] Appl. No.: 725,220

[22] Filed: Apr. 19, 1985

[51] Int. Cl.⁴ ............................................. A61N 1/36
[52] U.S. Cl. .................................. 128/419 D; 307/150
[58] Field of Search ................... 128/419 D, 711–712; 307/150; 312/111; 339/65, 66 R, 75 R, 76, 77, 198 GA, 198 H

[56] References Cited

U.S. PATENT DOCUMENTS

| D. 244,154 | 4/1977 | Smith et al. | D24/17 |
|---|---|---|---|
| D. 249,064 | 8/1978 | Smith et al. | D24/17 |
| D. 253,608 | 12/1979 | Smith et al. | D24/17 |
| D. 253,610 | 12/1979 | Smith et al. | D24/17 |
| 2,771,559 | 11/1956 | Montmeat | 307/156 |
| 3,552,817 | 1/1971 | Marcolongo | 312/111 |
| 3,865,101 | 2/1975 | Saper et al. | 128/419 D |
| 3,934,267 | 1/1976 | Kosaka et al. | 128/711 |
| 4,096,856 | 6/1978 | Smith et al. | 128/419 D |
| 4,097,113 | 6/1978 | McKelvy | 128/419 D |
| 4,300,087 | 11/1981 | Meisner | 307/150 |

FOREIGN PATENT DOCUMENTS 1496982 1/1978 United Kingdom ........... 128/419 D

OTHER PUBLICATIONS

Medical Research Laboratories, Inc., Technical Data Sheet, "Porta-Care MD-520 Monitor-Defibrillator", #995001.

Primary Examiner—William E. Kamm
Attorney, Agent, or Firm—Christensen, O'Connor, Johnson & Kindness

[57] ABSTRACT

A system for providing battery power to a portable defibrillator that includes a first housing having a generally vertical first sidewall (32). The system comprises battery pack (12) that includes a second housing having a second sidewall (38), battery means (80, 82) mounted within the second housing, and first electrical connector means (66) mounted in and extending through the second housing and electrically connected to the battery means. The system further comprises means forming grooves (46, 50) along the upper and lower edges of the first sidewall, and tongue means (40, 42) extending from the second sidewall, the tongue means being shaped to be slidingly received between the groove means to mount the battery pack to the defibrillator. A latch (68) is provided for latching the tongue means against lengthwise motion when the tongue means is received between the groove means. Second electrical connector means (62) are mounted adjacent the first sidewall between the groove means and is adapted to engage the first electrical connector means when the battery pack is mounted to the defibrillator. The battery pack may comprise rechargeable batteries and a battery charger (104) mounted within the second housing that is adapted to recharge the batteries upon the receipt of either an AC or a DC power signal.

7 Claims, 6 Drawing Figures

SYSTEM FOR PROVIDING POWER TO PORTABLE DEFIBRILLATOR

FIELD OF THE INVENTION

The present invention relates to defibrillators, and in particular to a system for providing power to a portable defibrillator.

BACKGROUND OF THE INVENTION

A defibrillator is a therapeutic medical instrument that is used to apply an electric shock to a patient in order to correct a cardiac arrhythmia such as ventricular fibrillation. When such an arrhythmia occurs, the heart is unable to pump a significant volume of blood, and serious brain damage and death will result unless a normal heart rhythm can be restored within a few minutes. By a mechanism not fully understood, an electric shock frequently terminates the chaotic activity characteristic of arrhythmias, and restores the normal pumping action of the heart.

Defibrillators have been known and successfully used for many years. However, many prior defibrillators have been nonportable instruments intended for use in connection with an ECG monitor to permit operator evaluation of the patient's heart rhythm. Defibrillators have recently been developed, however, that are capable of deriving an ECG signal from a patient through the defibrillator electrodes and analyzing the ECG signal to determine whether the patient has a heart rhythm that is subject to correction by defibrillation. Such defibrillators are therefore capable of advising an operator (e.g., a paramedic) that a defibrillation shock is or is not recommended.

The availability of a portable defibrillator having a shock advisory system represents a major advance in emergency health care. However, the effectiveness of such a defibrillator depends in significant measure on an effective system for supplying electrical power to the defibrillator. In the past, portable defibrillators have employed rechargeable battery packs that were inserted into a battery compartment within the defibrillator housing. When such a battery pack runs down, it may be removed from the defibrillator and recharged in an appropriate battery charger. This arrangement has certain limitations. The number of batteries that can be accommodated within the housing of a portable defibrillator is quite limited, therefore resulting in a defibrillator which can deliver a limited number of defibrillation shocks before battery replacement or recharging is required. In the past, this problem has typically been addressed through the use of high-capacity nickel-cadmium batteries. Unfortunately, nickel-cadmium batteries have a comparatively short shelf life after a recharge, a fact that reduces the effectiveness of recharging procedures and increases battery supply costs.

SUMMARY OF THE INVENTION

The present invention provides a system for supply battery power to a portable defibrillator. The defibrillator comprises a first housing having a generally vertical first sidewall. The battery supply system comprises a battery pack that includes a second housing having a second sidewall, battery means mounted within the second housing, and first electrical connector means. The first electrical connector means is mounted in and extends through the second housing, and is electrically connected to te battery means. The battery supply system further includes upper and lower groove means extending along the upper and lower edges of the first sidewall and respectively forming downwardly and upwardly facing horizontal grooves. Tongue means extend from the second sidewall and is shaped to be slidingly received between the upper and lower groove means to mount the battery pack to the defibrillator. Latch means are provided for latching the tongue means against lengthwise motion when the tongue means is received between the upper and lower groove means. The battery supply system further comprises second electrical connector means mounted adjacent the first sidewall between the upper and lower groove means and adapted to engage the first electrical connector means when the battery pack is mounted to the defibrillator. The battery pack may comprise rechargeable batteries and a battery charger mounted within the second housing adapted to recharge the rechargeable batteries upon receipt of either an AC or a DC power signal. The second electrical connector means may comprise a connector assembly mounted adjacent the rearmost edge of the first sidewall and comprising a pair of forwardly projecting conductive pins. The tongue means may likewise include a cutaway section adjacent the rearmost edge of the second sidewall, and the first electrical connector means may comprise a pair of sockets. The cutaway section and sockets are dimensionsed and positioned to receive the connector assembly and pins, respectively, when the battery pack is mounted to the defibrillator.

DETAILED DESCRIPTION

Figure 1:
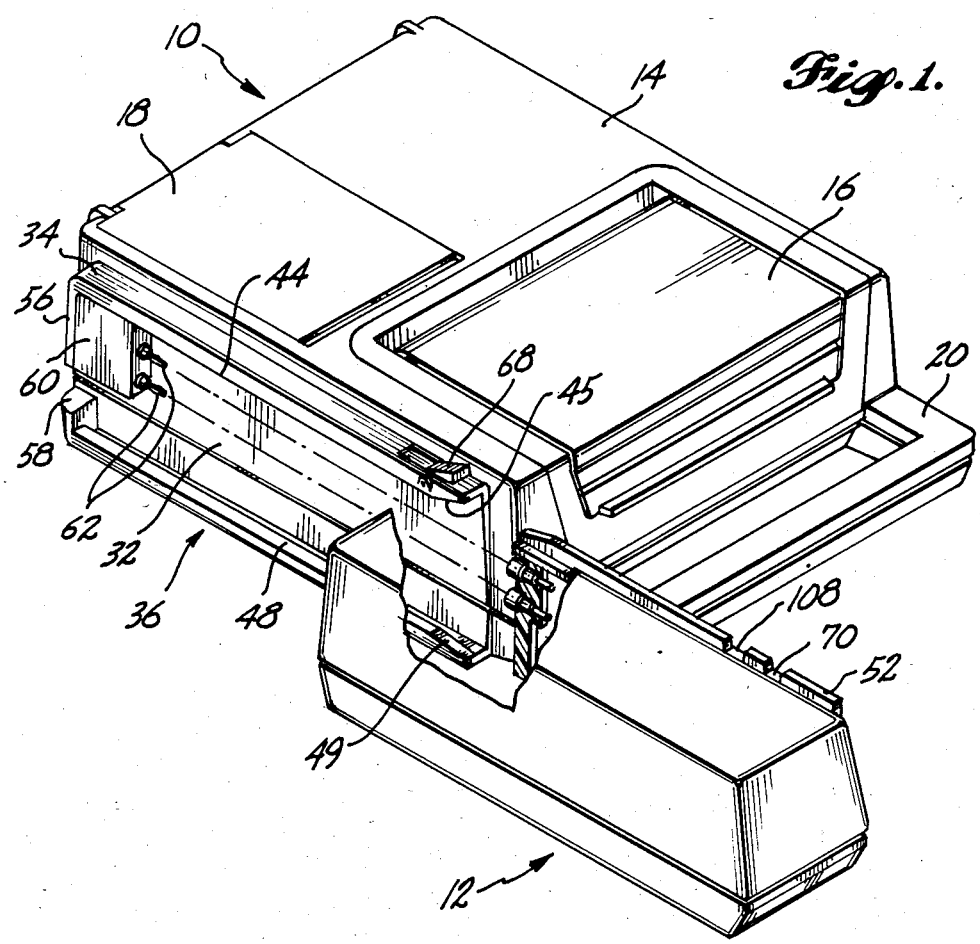
FIG. 1 is a perspective view of a defibrillator and a battery pack that may be externally connected to the defibrillator according to the system of the present invention.
Figure 2:
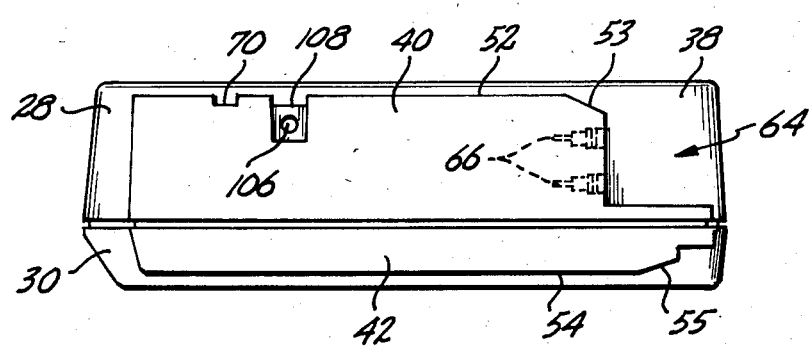
FIG. 2 is a side elevational view of the battery pack.

FIG. 1 illustrates a battery power supply system for portable defibrillator 10. The power supply system comprises battery pack 12 that is externally connectable to the defibrillator. Defibrillator 10 includes body 14, display module 16, compartment 18 and handle 20. Display module 16 is adapted to rotate from its closed position, illustrated in FIG. 1, to an open position in which the display module rotates upward and rearward to bring a display screen and a set of switches into view for use by the operator. Compartment 18 is used for storing the cables through which the defibrillator may be connected to patient engaging electrodes.

Referring now to FIGS. 1–4, body 14 of defibrillator 10 comprises upper housing 24 and lower housing 26 that are joined and sealed together. Likewise, battery pack 12 comprises upper housing 28 and lower housing 30 that are joined and sealed together. Side 32 of defibrillator 10 comprises upper groove member 34 and lower groove member 36, the groove members extending laterally from upper housing 24 and lower housing 26 respectively. Side 38 of battery pack 12 includes upper tongue member 40 and lower tongue member 42, the tongue members extending laterally from upper housing 28 and lower housing 30 respectively. Battery pack 12 is dimensioned such that side 38 has approximately the same height and length as side 32. Groove members 34 and 36 extend along essentially the entire length of side 32, and tongue members 40 and 42 extend along essentially the entire length of side 38.

Upper groove member 34 includes depending lip 44 that forms groove 46, the forward end of lip 44 comprising angled section 45. Lower groove member 36 includes upwardly extending lip 48 that forms groove 50, the forward end of lip 48 comprising angled section 49. Upper tongue member 40 includes upwardly extending tongue 52, and lower tongue member 42 includes downwardly extending tongue 54. The rearward ends of tongues 52 and 54 comprise angled sections 53 and 55 respectively. End portions 56 and 58 border the rearmost edge of side 32. Connector assembly 60 is mounted to side 32 just forward of end portion 56, connector assembly 60 comprising conductive pins 62 that extend in a forward direction from the connector assembly. The rearmost section of upper tongue member 40 includes cut-away section 64, the size of the cut-away section corresponding to the size of connector assembly 60. Electrical sockets 66 are mounted in upper tongue member 40 such that the sockets face rearwardly into cut-away portion 64. Sockets 66 are adapted to mate with pins 62, as described below.

The battery pack is connected to the defibrillator by inserting tongues 52 and 54 into the forward edges of grooves 46 and 48, respectively, such insertion being facilitated by angled sections 45, 49, 53 and 55. Groove members 34 and 36 and tongue members 40 and 42 are dimensioned such that the tongue members can be slid in forward and rearward directions in the groove members with a sliding fit such that when the tongue members are received in the groove members, the battery pack is not free to rotate or to move in up and down or side-to-side directions with respect to the defibrillator. When the tongues are fully inserted into the grooves, pins 62 of defibrillator 10 extend into sockets 66 of battery pack 12 to thereby establish electrical connection between the defibrillator and battery pack. The battery pack is latched in this fully connected position by a latching mechanism that comprises latch arm 68 mounted in upper groove member 34 and notch 70 in tongue 52. The latch arm is mounted for pivotal movement about pivot pin 78, the latch arm including lug 72 that extends downwardly from the latch arm into groove 46. When the battery pack is fully connected to the defibrillator, lug 72 is received in notch 70, thereby latching the battery pack to the defibrillator. The lug is held in notch 70 by spring 74 that tends to rotate latch arm 68 about pivot pin 78 in a counterclockwise direction as viewed in FIG. 4. To remove the battery pack, an operator rotates the forward end 76 of latch arm 68 downwardly against the force of spring 74, to thereby move lug 72 upward out of notch 70. The battery pack can then be slid in a forward direction with respect to the defibrillator to remove the battery pack. The insertion of tongue 52 into groove 46 past lug 72 is facilitated by angled section 53 of tongue 52. The ease and simplicity with which the battery pack can be connected and disconnected represents a significant improvement over prior battery systems for defibrillators.

Figure 3:
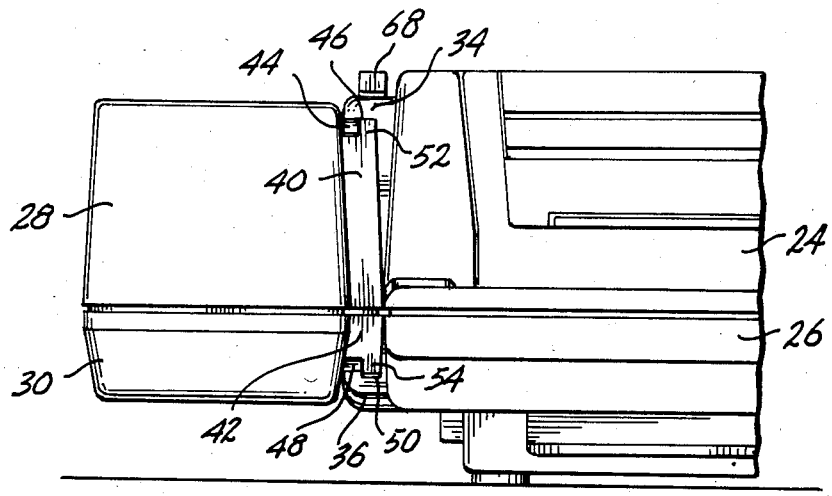
FIG. 3 is a partial front elevational view of the defibrillator and battery pack connected to one another.
Figure 4:
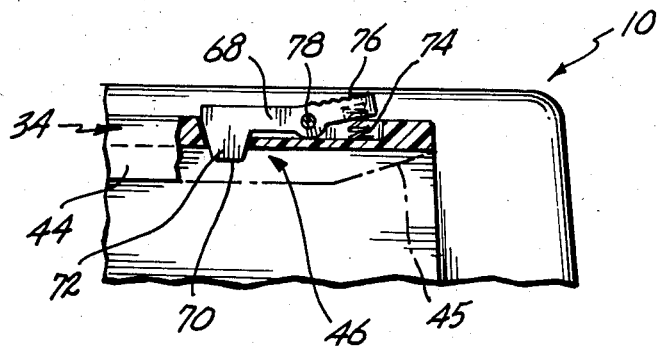
FIG. 4 is a partial side elevational view of the defibrillator showing the latch arm.

FIG. 3 illustrates that when the battery pack is mounted to side 32 of defibrillator 10, the battery pack is supported by the defibrillator in a cantilevered fashion, such that the battery pack extends outward from side 32 without contacting the support surface upon which the defibrillator is positioned. When the battery pack is so mounted, it increases the width of the instrument without adding to its height or to its length. The battery system of the present invention therefore provides much of the compactness of an internally mounted battery pack, without the capacity, access or contamination limitations that are inherent in the internal mounting arrangement.

Figure 5:
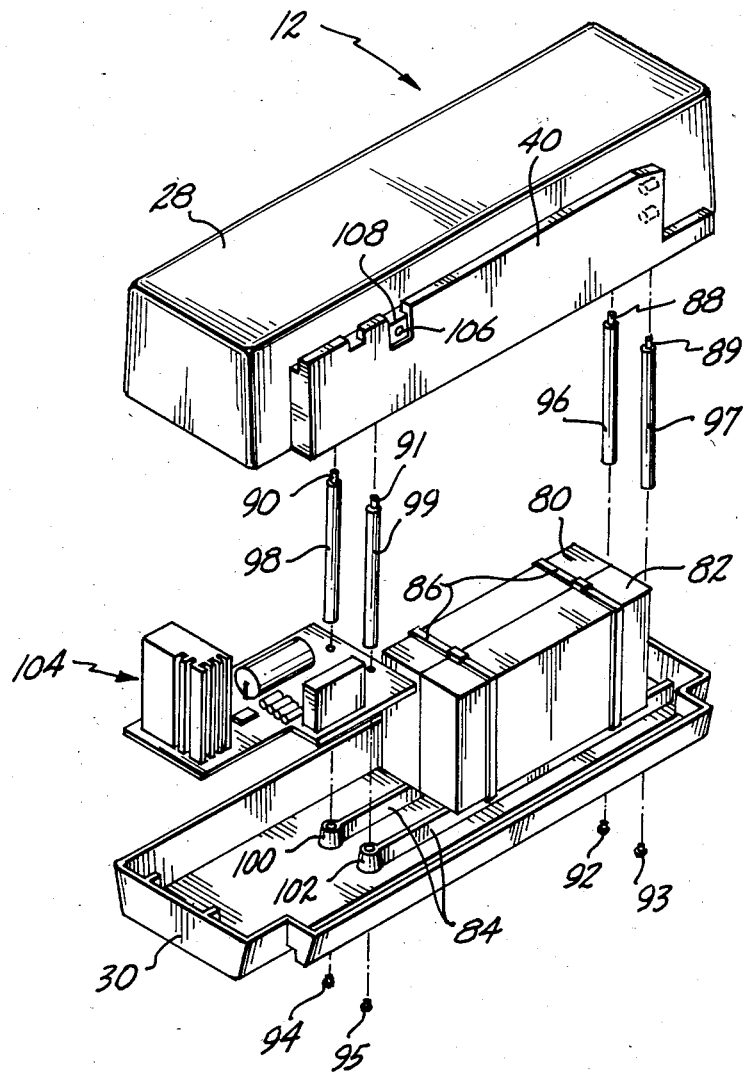
FIG. 5 is an exploded perspective view of the battery pack.

Referring now to FIG. 5, battery pack 12 in one preferred arrangement comprises battery pack modules 80 and 82 and battery charger 104. Each module comprises four lead-acid batteries, and the modules are connected in series to produce a total supply voltage of approximately 16.5 volts. This high supply voltage (compared to prior portable defibrillators) results in a number of significant advantages, including a reduction in the current required to charge the defibrillator energy storage means to a specified power level. The lower current in turn makes it possible to reduce the size of the transformer and other components of the defibrillator charging circuit, to produce a more compact and portable instrument.

Figure 6:
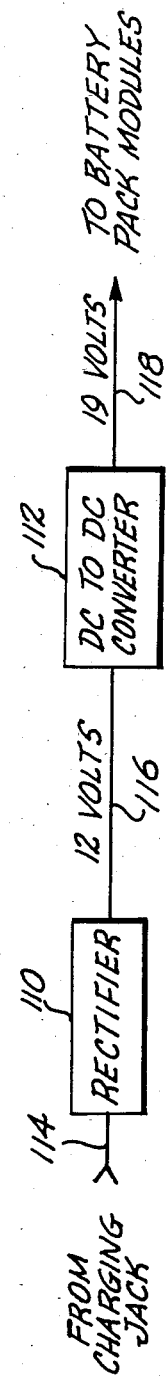
FIG. 6 is a block diagram of the battery charger.

The battery pack modules are mounted on rails 84 that extend upward from lower housing 30. The battery pack modules are secured to the rails by ties 86. Upper housing 28 is joined to lower housing 30 by means of shafts 88-91, bolts 92-95 and stand-offs 96-99. Shafts 90 and 91 extend through pedestals 100 and 102 respectively, and serve to mount battery charger 104. Battery charger 104 is preferably adapted to recharge the batteries of battery pack modules 80 and 82 from a 12 volt DC source, such as an automobile ignition system, as well as from an AC source. In both cases the charging source is coupled to the battery charger through charging jack 106 that is positioned within recess 108 in upper tongue member 40. A preferred battery charger is indicated schematically in FIG. 6 as comprising rectifier 110 and DC-to-DC converter 112. Rectifier 110 receives a power signal (AC or DC) through charging jack 106 and line 114, and rectifies the signal to produce a 12 volt output signal on line 116. When the signal on line 114 is a 12 volt DC signal, such signal is simply passed through rectifier 110 to line 116. When the signal on line 114 is a 10 volt AC signal, such signal is rectified to produce a 12 volt DC signal on line 116. Such a 10 volt AC signal may conveniently be provided through a transformer adapted to be mounted in a normal 110 volt AC electrical wall socket. The 12 volt signal on line 116 is stepped-up to a level of approximately 19 volts to DC-to-DC converter 112, the resulting 19 volt signal being output on line 118 and coupled by conventional means to the serial connected battery pack modules. The capacity to receive either an AC or DC power signal significantly enhances the usefulness and versatility of the defibrillator and its associated power supply system, particularly in connection with its use in aid cars and related emergency medical services.

While the preferred embodiments of the invention have been illustrated and described, it should be understood that variations will be apparent to those skilled in the art. Accordingly, the invention is not to be limited to the specific embodiments illustrated and described, and the true scope and spirit of the invention are to be determined by reference to the following claims.

The embodiments of the invention in which an exclusive property or privilege is claimed are defined as follows:

1. A system for providing battery power to a portable defibrillator that comprises a first housing having a generally vertical first sidewall, the system comprising:
   (a) a battery pack including a second housing having a second sidewall, battery means mounted within the second housing, and first electrical connector means mounted in and extending through the second housing and electrically connected to the battery means;
   (b) upper groove means extending along the upper edge of the first sidewall and forming a downwardly facing horizontal groove;
   (c) lower groove means extending along the lower edge of the first sidewall and forming an upwardly facing horizontal groove;
   (d) tongue means extending from the second sidewall and shaped to be slidingly received between the upper and lower groove means to mount the battery pack to the defibrillator;
   (e) latch means for latching the tongue means against lengthwise motion when the tongue means is received between the upper and lower groove means;
   (f) second electrical connector means extending from the first sidewall between the upper and lower groove means and adapted to engage the first electrical connector means when the battery pack is mounted to the defibrillator.

2. The system of claim 1, wherein the battery means comprises rechargeable battery means, and wherein the battery pack includes a battery charger mounted within the second housing and a charging jack extending through the second housing and electrically connected to the battery charger.

3. The system of claim 2, wherein the battery charger is adapted to recharge the rechargeable battery means upon receipt of either an AC or a DC power signal through the charging jack.

4. The system of claim 3, wherein the dimensions of the battery pack and defibrillator are approximately equal in directions parallel to the first surface.

5. The system of claim 2, wherein the second electrical connector means comprises a connector assembly mounted adjacent the rearmost edge of the first sidewall, the connector assembly comprising a pair of forwardly projecting conductive pins.

6. The system of claim 5, wherein the tongue means includes a cut-away section adjacent the rearmost edge of the second sidewall, and wherein the first electrical connector means comprises a pair of sockets, the cut-away section and sockets being dimensioned and positioned to receive the connector assembly and pins respectively when the battery pack is mounted to the defibrillator.

7. The system of claim 1, wherein the battery pack is supported entirely through the tongue means when the battery pack is mounted to the defibrillator, such that the battery pack is mounted in a cantilevered fashion from the first sidewall.

* * * * *

UNITED STATES PATENT AND TRADEMARK OFFICE
CERTIFICATE OF CORRECTION

PATENT NO. : 4,590,943
DATED : May 27, 1986
INVENTOR(S) : Paull et al.

It is certified that error appears in the above-identified patent and that said Letters Patent is hereby corrected as shown below:

Column 1, line 59, "supply" is changed to --supplying--
          line 68, "te" is changed to --the--
Column 2, line 27, "dimensionsed" is changed to --dimensioned--
Column 3, line 32, "48" is changed to --50--

Signed and Sealed this

Second Day of September 1986

[SEAL]

Attest:

DONALD J. QUIGG

Attesting Officer    Commissioner of Patents and Trademarks